(12) United States Patent
Rostami et al.

(10) Patent No.: US 10,420,859 B2
(45) Date of Patent: Sep. 24, 2019

(54) FLUSHABLE CATHETERS

(71) Applicant: Hollister Incorporated, Libertyville, IL (US)

(72) Inventors: Shamsedin Rostami, South Cambridgeshire (GB); Adam J. Foley, Swords (IE); John T. Clarke, Galway (IE); Horacio Montes de Oca Balderas, Ballina (IE); Enda F. Carter, Ballina (IE); Jerome A. Henry, Castlebar (IE)

(73) Assignee: Hollister Incorporated, Libertyville, IL (US)

( * ) Notice: Subject to any disclaimer, the term of this patent is extended or adjusted under 35 U.S.C. 154(b) by 260 days.

(21) Appl. No.: 15/102,322

(22) PCT Filed: Dec. 10, 2014

(86) PCT No.: PCT/US2014/069569
§ 371 (c)(1),
(2) Date: Jun. 7, 2016

(87) PCT Pub. No.: WO2015/089197
PCT Pub. Date: Jun. 18, 2015

(65) Prior Publication Data
US 2016/0317715 A1 Nov. 3, 2016

Related U.S. Application Data

(60) Provisional application No. 62/011,282, filed on Jun. 12, 2014, provisional application No. 61/915,382, (Continued)

(51) Int. Cl.
*A61M 25/00* (2006.01)
*A61L 29/04* (2006.01)
*A61L 29/14* (2006.01)

(52) U.S. Cl.
CPC ............. *A61L 29/041* (2013.01); *A61L 29/04* (2013.01); *A61L 29/14* (2013.01);
(Continued)

(58) Field of Classification Search
CPC .... A61L 2400/10; A61L 29/04; A61L 29/041; A61L 29/14; A61M 2025/0046; A61M 25/0017; A61M 25/0045
See application file for complete search history.

(56) References Cited

U.S. PATENT DOCUMENTS 2,509,241 A * 5/1950 Mende ................... A61F 13/26
604/11
3,583,391 A 6/1971 Cox et al.
(Continued)

FOREIGN PATENT DOCUMENTS

CN 2240371 11/1996
CN 101300036 A 11/2008
(Continued)

OTHER PUBLICATIONS

Rachna N. Dave, Hiren M. Joshi, and Vayalam P. Benugopalan, Novel Biocatalytic Polymer-Based Antimicrobial Coatings as Potential Ureteral Biomaterial, Feb. 1, 2011, 44(2): 845-853.
(Continued)

*Primary Examiner* — Adam Marcetich
(74) *Attorney, Agent, or Firm* — Cook Alex Ltd.

(57) ABSTRACT

A flushable catheter assembly that includes at least one shrinkable portion that shrinks from a first configuration to a second compact configuration to reduce the size of the catheter assembly for passage through the sewer system. The flushable catheter may also be made from a water disintegratable polymer that dissolves, degrades or hydrolyzes while within the sewer system.

20 Claims, 10 Drawing Sheets

Related U.S. Application Data filed on Dec. 12, 2013, provisional application No. 61/915,396, filed on Dec. 12, 2013.

(52) U.S. Cl.
CPC .... *A61M 25/0017* (2013.01); *A61M 25/0045* (2013.01); *A61L 2400/10* (2013.01); *A61M 2025/0046* (2013.01)

(56) References Cited

U.S. PATENT DOCUMENTS

| | | | |
|---|---|---|---|
| 3,621,848 A | 11/1971 | Magovern | |
| 3,702,610 A | 11/1972 | Sheppard et al. | |
| 3,861,396 A | 1/1975 | Vaillancourt et al. | |
| 3,894,540 A | 7/1975 | Bonner, Jr. | |
| 3,971,367 A * | 7/1976 | Zaffaroni | A61F 6/144 |
| | | | 128/833 |
| 4,062,363 A | 12/1977 | Bonner, Jr. | |
| 4,100,309 A | 7/1978 | Micklus et al. | |
| 4,227,533 A | 10/1980 | Godfrey | |
| 4,413,986 A | 11/1983 | Jacobs | |
| 4,465,481 A | 8/1984 | Blake | |
| 4,610,671 A | 9/1986 | Luther | |
| 4,668,221 A | 5/1987 | Luther | |
| 4,762,738 A | 8/1988 | Keyes et al. | |
| 4,769,005 A | 9/1988 | Ginsburg et al. | |
| 4,772,279 A | 9/1988 | Brooks et al. | |
| 4,790,817 A | 12/1988 | Luther | |
| 4,790,831 A | 12/1988 | Skribiski | |
| 4,795,439 A | 1/1989 | Guest | |
| 4,834,733 A * | 5/1989 | Huntoon | A61F 13/42 |
| | | | 604/361 |
| 4,840,622 A | 6/1989 | Hardy | |
| 4,883,699 A | 11/1989 | Aniuk et al. | |
| 4,906,238 A | 3/1990 | Greenfeld et al. | |
| 4,930,942 A * | 6/1990 | Keyes | A61F 5/445 |
| | | | 406/49 |
| 4,952,359 A | 8/1990 | Wells | |
| 4,954,129 A | 9/1990 | Giuliani et al. | |
| 4,994,047 A | 2/1991 | Walker et al. | |
| 5,002,526 A | 3/1991 | Herring | |
| 5,009,648 A | 4/1991 | Aronoff et al. | |
| 5,089,535 A | 2/1992 | Malwitz et al. | |
| 5,098,535 A | 3/1992 | Nakakoshi et al. | |
| 5,102,401 A | 4/1992 | Lambert et al. | |
| 5,195,962 A | 3/1993 | Martin et al. | |
| 5,270,086 A | 12/1993 | Hamlin | |
| 5,346,468 A * | 9/1994 | Campion | A61F 13/26 |
| | | | 604/13 |
| 5,439,454 A | 8/1995 | Lo et al. | |
| 5,444,113 A * | 8/1995 | Sinclair | A61L 15/26 |
| | | | 524/306 |
| 5,468,526 A | 11/1995 | Allen et al. | |
| 5,472,417 A | 12/1995 | Martin et al. | |
| 5,569,219 A | 10/1996 | Hakki et al. | |
| 5,601,538 A | 2/1997 | Deem | |
| 5,616,126 A | 4/1997 | Malekmehr et al. | |
| 5,641,562 A * | 6/1997 | Larson | A61L 15/225 |
| | | | 442/394 |
| 5,681,299 A * | 10/1997 | Brown | A61F 13/15211 |
| | | | 604/358 |
| 5,688,459 A | 11/1997 | Mao et al. | |
| 5,776,611 A | 7/1998 | Elton et al. | |
| 5,792,114 A | 8/1998 | Fiore | |
| 5,800,412 A | 9/1998 | Zhang et al. | |
| 5,804,653 A | 9/1998 | Weng | |
| 5,904,703 A | 5/1999 | Gilson | |
| 5,985,394 A | 11/1999 | Mao et al. | |
| 6,017,334 A | 1/2000 | Rawls | |
| 6,030,369 A | 2/2000 | Engelson et al. | |
| 6,060,534 A * | 5/2000 | Ronan | A61L 29/145 |
| | | | 424/422 |
| 6,063,063 A | 5/2000 | Harboe et al. | |
| 6,066,120 A | 5/2000 | Whiteside | |
| 6,071,618 A | 6/2000 | Cook, Jr. et al. | |
| 6,090,075 A | 7/2000 | House | |
| 6,213,990 B1 | 4/2001 | Roempke | |
| 6,217,562 B1 * | 4/2001 | Brown | A61F 5/44 |
| | | | 604/317 |
| 6,217,569 B1 | 4/2001 | Fiore | |
| 6,447,835 B1 | 9/2002 | Wang et al. | |
| 6,468,245 B2 | 10/2002 | Alexandersen | |
| 6,471,684 B2 | 10/2002 | Dulak et al. | |
| 6,488,659 B1 | 12/2002 | Rosenman | |
| 6,552,123 B1 * | 4/2003 | Katayama | D01F 6/34 |
| | | | 264/172.17 |
| 6,562,443 B1 * | 5/2003 | Espinel | B32B 27/08 |
| | | | 156/244.24 |
| 6,585,721 B2 | 7/2003 | Fiore | |
| 6,627,586 B1 | 9/2003 | Brooks et al. | |
| 6,656,146 B1 | 12/2003 | Clayman et al. | |
| 6,664,333 B2 | 12/2003 | Wang et al. | |
| 6,713,140 B2 | 3/2004 | McCormack et al. | |
| 6,726,654 B2 | 4/2004 | Rosenman | |
| 6,942,635 B2 | 9/2005 | Rosenblatt et al. | |
| 6,960,224 B2 | 11/2005 | Marino et al. | |
| 6,976,973 B1 | 12/2005 | Ruddell et al. | |
| 7,037,295 B2 | 5/2006 | Tiernan et al. | |
| 7,128,862 B2 | 10/2006 | Wang | |
| 7,156,824 B2 | 1/2007 | Rosenman | |
| 7,182,906 B2 | 2/2007 | Chen | |
| 7,402,620 B2 | 7/2008 | McGhee | |
| 7,553,923 B2 | 6/2009 | Williams | |
| 7,601,158 B2 | 10/2009 | Ouse | |
| 7,641,757 B2 | 1/2010 | Kampa et al. | |
| 7,662,146 B2 | 2/2010 | House | |
| 7,731,740 B2 | 6/2010 | LaFont et al. | |
| 7,789,873 B2 | 9/2010 | Kubalak et al. | |
| 7,815,628 B2 | 10/2010 | Devens, Jr. | |
| 7,820,284 B2 | 10/2010 | Terry | |
| 7,824,517 B2 | 11/2010 | Kampa et al. | |
| 7,833,280 B2 | 11/2010 | Stack et al. | |
| 7,947,031 B2 | 5/2011 | DiMatteo et al. | |
| 8,143,368 B2 | 3/2012 | Domb et al. | |
| 8,168,249 B2 | 5/2012 | Utas et al. | |
| 8,187,254 B2 | 5/2012 | Hissink | |
| 8,388,583 B2 | 3/2013 | Stout | |
| 8,388,585 B2 | 3/2013 | Tomes | |
| 8,469,928 B2 | 6/2013 | Stout | |
| 8,518,019 B2 | 8/2013 | Green | |
| 8,569,402 B2 | 10/2013 | Henderson et al. | |
| 2001/0053646 A1 * | 12/2001 | Tanaka | D01D 5/24 |
| | | | 442/181 |
| 2002/0016574 A1 | 2/2002 | Wang et al. | |
| 2002/0128625 A1 * | 9/2002 | Tanaka | A61F 13/4752 |
| | | | 604/385.28 |
| 2003/0036721 A1 * | 2/2003 | Zhao | A61F 13/26 |
| | | | 604/15 |
| 2003/0060793 A1 * | 3/2003 | Topolkaraev | A61F 13/15203 |
| | | | 604/385.29 |
| 2003/0165647 A1 | 9/2003 | Kaneko et al. | |
| 2003/0187368 A1 | 10/2003 | Sata et al. | |
| 2003/0228434 A1 | 12/2003 | Bailey et al. | |
| 2004/0030376 A1 * | 2/2004 | Gibson | A61N 1/0541 |
| | | | 607/137 |
| 2004/0122382 A1 | 6/2004 | Johnson et al. | |
| 2004/0210180 A1 | 10/2004 | Altman | |
| 2004/0023258 A1 | 11/2004 | Kawabata et al. | |
| 2004/0220550 A1 | 11/2004 | Schryver | |
| 2004/0230177 A1 | 11/2004 | DiMatteo et al. | |
| 2005/0031833 A1 * | 2/2005 | Dilnik | A47K 7/02 |
| | | | 428/181 |
| 2005/0049577 A1 | 3/2005 | Snell et al. | |
| 2005/0109648 A1 | 5/2005 | Kerzman et al. | |
| 2005/0131386 A1 | 6/2005 | Freeman et al. | |
| 2005/0163844 A1 | 7/2005 | Ashton | |
| 2005/0197627 A1 | 9/2005 | Huang et al. | |
| 2005/0218154 A1 | 10/2005 | Selsby | |
| 2005/0277862 A1 | 12/2005 | Anand | |
| 2005/0283111 A1 | 12/2005 | Maurice | |
| 2006/0173422 A1 | 8/2006 | Reydel et al. | |
| 2006/0240064 A9 | 10/2006 | Hunter et al. | |

(56) References Cited

U.S. PATENT DOCUMENTS

| | | |
|---|---|---|
| 2007/0043333 A1 | 2/2007 | Kampa et al. |
| 2007/0078412 A1 | 4/2007 | McGuckin, Jr. et al. |
| 2007/0088330 A1 | 4/2007 | House |
| 2007/0203502 A1 | 8/2007 | Makker et al. |
| 2007/0225649 A1 | 9/2007 | House |
| 2008/0015527 A1 | 1/2008 | House |
| 2008/0091145 A1 | 4/2008 | House |
| 2008/0097411 A1 | 4/2008 | House |
| 2008/0118544 A1 | 5/2008 | Wang |
| 2008/0147049 A1 | 6/2008 | House et al. |
| 2008/0171991 A1 | 7/2008 | Kourakis |
| 2008/0171998 A1 | 7/2008 | House |
| 2008/0172042 A1 | 7/2008 | House |
| 2008/0183262 A1 | 7/2008 | Dowling |
| 2008/0255510 A1 | 10/2008 | Wang |
| 2008/0260917 A1* | 10/2008 | Sankey .............. B32B 3/10 426/114 |
| 2008/0268193 A1 | 10/2008 | Cherry et al. |
| 2008/0292776 A1 | 11/2008 | Dias et al. |
| 2008/0312550 A1 | 12/2008 | Nishtala |
| 2009/0018530 A1 | 1/2009 | Nielsen et al. |
| 2009/0036874 A1 | 2/2009 | Horowitz et al. |
| 2009/0084321 A1* | 4/2009 | Mo .................. B65F 1/0006 119/161 |
| 2009/0250370 A1 | 10/2009 | Whitchurch |
| 2009/0264869 A1 | 10/2009 | Schmid et al. |
| 2009/0278279 A1* | 11/2009 | Uradnisheck ....... B29C 51/428 264/210.1 |
| 2009/0286031 A1* | 11/2009 | Shi ................. A61F 13/15211 428/41.8 |
| 2009/0306767 A1* | 12/2009 | Lendlein ............ B29C 61/065 623/1.18 |
| 2010/0030197 A1 | 2/2010 | House |
| 2010/0049146 A1 | 2/2010 | Nielsen et al. |
| 2010/0098746 A1 | 4/2010 | King |
| 2010/0100116 A1 | 4/2010 | Brister et al. |
| 2010/0137743 A1 | 6/2010 | Nishtala et al. |
| 2010/0145315 A1 | 6/2010 | House |
| 2010/0159768 A1* | 6/2010 | Lee .................. B29C 44/357 442/189 |
| 2010/0198195 A1 | 8/2010 | Nishtala et al. |
| 2010/0204682 A1 | 8/2010 | Tanghoj et al. |
| 2010/0209472 A1 | 8/2010 | Wang |
| 2010/0215708 A1 | 8/2010 | Zumbuehl et al. |
| 2010/0279057 A1* | 11/2010 | Zafiroglu ............ B32B 5/02 428/86 |
| 2010/0312255 A1 | 12/2010 | Satake et al. |
| 2010/0323189 A1 | 12/2010 | Illsley et al. |
| 2011/0049146 A1 | 3/2011 | Illsley et al. |
| 2011/0071507 A1 | 3/2011 | Svensson et al. |
| 2011/0114520 A1 | 5/2011 | Matthison-Hansen |
| 2011/0125135 A1 | 5/2011 | Ahmed |
| 2011/0160662 A1 | 6/2011 | Stout |
| 2011/0178425 A1 | 7/2011 | Nishtala |
| 2011/0212157 A1 | 9/2011 | Edelson et al. |
| 2011/0218472 A1* | 9/2011 | Mirzadeh ............ A61F 13/0259 602/43 |
| 2011/0238163 A1 | 9/2011 | Andrews et al. |
| 2011/0268938 A1 | 11/2011 | Schuhmann |
| 2012/0035530 A1 | 2/2012 | Wang |
| 2012/0121919 A1 | 5/2012 | Nielsen |
| 2012/0296303 A1* | 11/2012 | Ng ................. A61F 13/47263 604/378 |
| 2013/0131646 A1 | 5/2013 | Gilman |
| 2013/0319288 A1* | 12/2013 | Belcheva .............. C08L 1/02 106/163.01 |
| 2013/0345681 A1 | 12/2013 | Hong |
| 2014/0066874 A1* | 3/2014 | Hopkins ............ A61F 13/539 604/378 |
| 2015/0119967 A1* | 4/2015 | Pawsey ............ A61N 1/36036 607/137 |

FOREIGN PATENT DOCUMENTS

| | | |
|---|---|---|
| DE | 10 2011 11916 A1 | 5/2013 |
| EP | 0010171 A1 | 4/1980 |
| EP | 0166998 B1 | 1/1986 |
| EP | 0613672 A1 | 9/1994 |
| EP | 0628586 B1 | 12/1994 |
| EP | 0692276 A2 | 1/1996 |
| EP | 1062920 A1 | 12/2000 |
| EP | 1110561 A2 | 6/2001 |
| EP | 1415671 A1 | 5/2004 |
| EP | 2026846 A1 | 2/2009 |
| EP | 2301595 A1 | 3/2011 |
| EP | 2520412 A1 | 11/2012 |
| EP | 2609956 A1 | 7/2013 |
| GB | 2083762 | 3/1982 |
| GB | 2496901 A | 5/2013 |
| JP | S-61209655 A | 9/1986 |
| JP | 01-136662 | 9/1989 |
| JP | 11151293 | 6/1999 |
| KR | 2000/065291 A | 11/2000 |
| KR | 100754057 B | 8/2007 |
| WO | WO 89/05671 A | 6/1989 |
| WO | WO 96/41653 A1 | 12/1996 |
| WO | WO 1998/058989 A1 | 12/1998 |
| WO | WO 00/30696 A1 | 6/2000 |
| WO | WO 2006/055847 A2 | 5/2006 |
| WO | WO 2006/071813 A2 | 7/2006 |
| WO | WO 2007/122269 A1 | 11/2007 |
| WO | WO 2007/140320 A2 | 12/2007 |
| WO | WO 2010/043565 A1 | 4/2010 |
| WO | WO 2011/076211 A1 | 6/2011 |
| WO | WO 2012/163413 A1 | 12/2012 |
| WO | WO 2012/166967 A1 | 12/2012 |
| WO | WO 2014/193402 A1 | 12/2014 |

OTHER PUBLICATIONS

Beom Soo Kim, Jeffrey S. Hrkach, Robert Langer, Biodegradable photo-crosslinked poly(ether-ester) networks for lubricious coatings, Biomaterials, vol. 21, Issue 3, Feb. 2000, pp. 259-265.
A.K. Singla, M. Chawla, Chitosan some pharmaceutical and biological aspects, an update, Journal of Pharmacy and Pharmacology, Aug. 2001, 53: 1047-1067.
FreeStyle Vie Flushable Colostomy Bag by CliniMed Ltd., retrieved from http://www.clinimed.co.uk/Stoma-Care/Products/Closed-Stoma-Bags/Freestyle-Vie-Flushable/Product-Design.aspx Jan. 1, 2014.
International Search Report and Written Opinion dated Jun. 10, 2015, for International Application No. PCT/US2014/069569.
IP Australia Examination report No. 1 for standard patent application dated Oct. 12, 2017 for Application No. 2014362368.
IP Australia Examination report No. 2 for standard patent application dated Jul. 11, 2018 for Application No. 2014362368.
IP Australia Examination report No. 3 for standard patent application dated Aug. 22, 2018 for Application No. 2014362368.

* cited by examiner

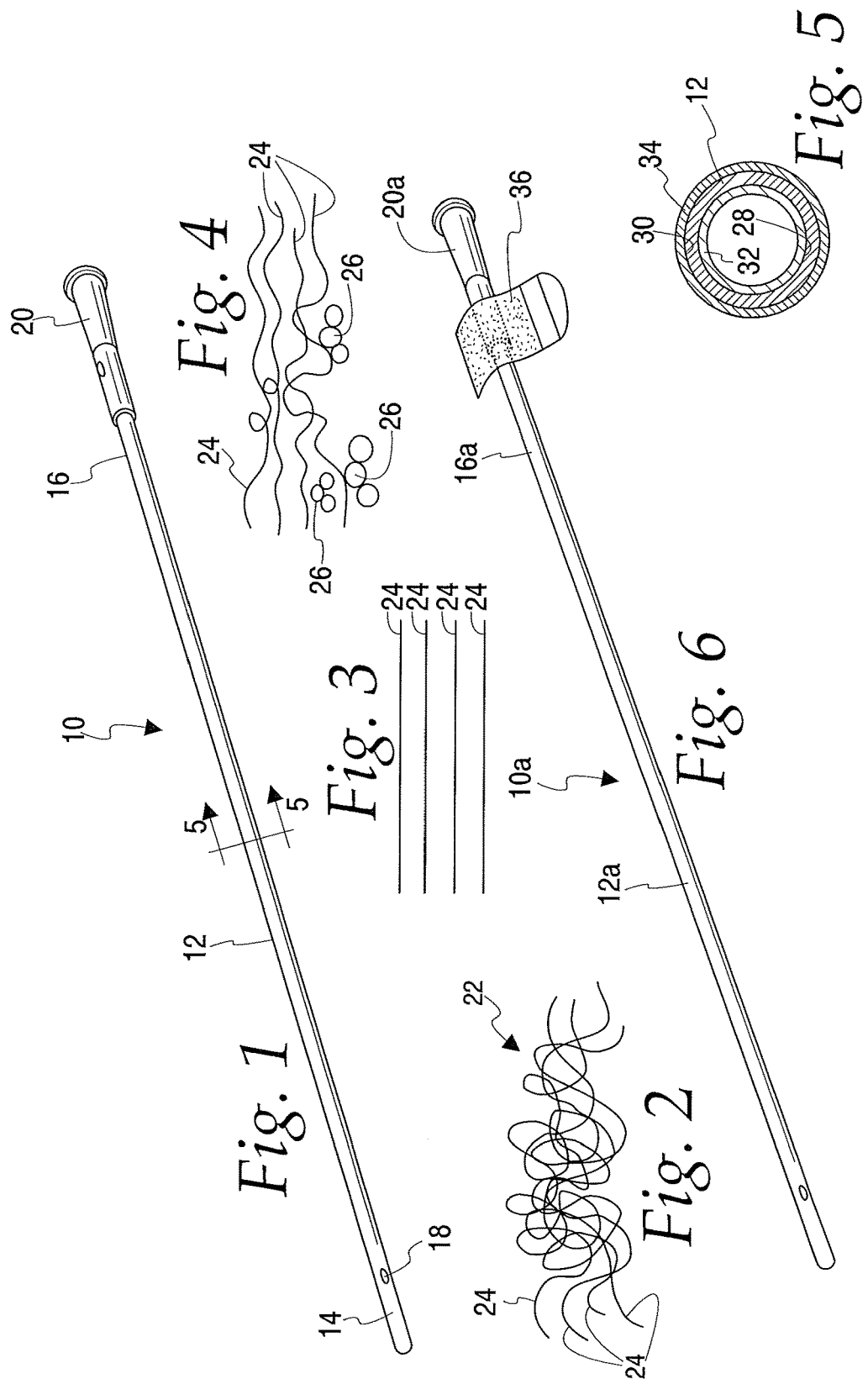

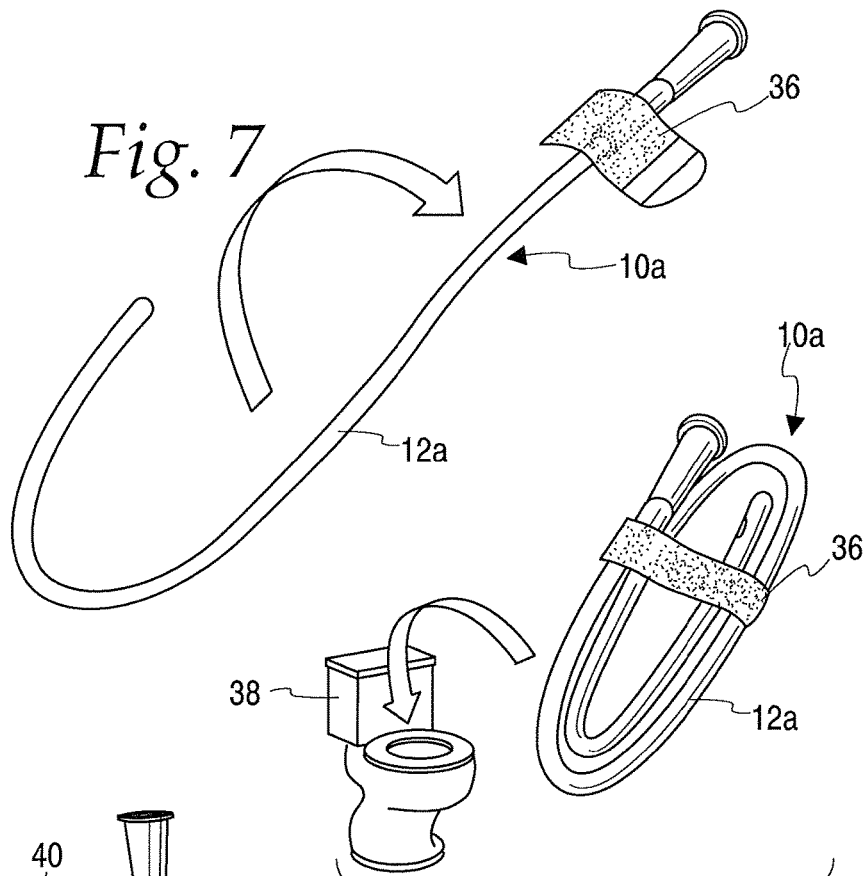
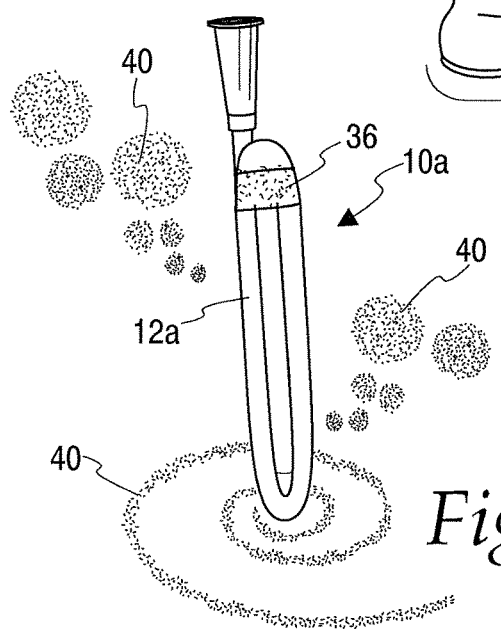

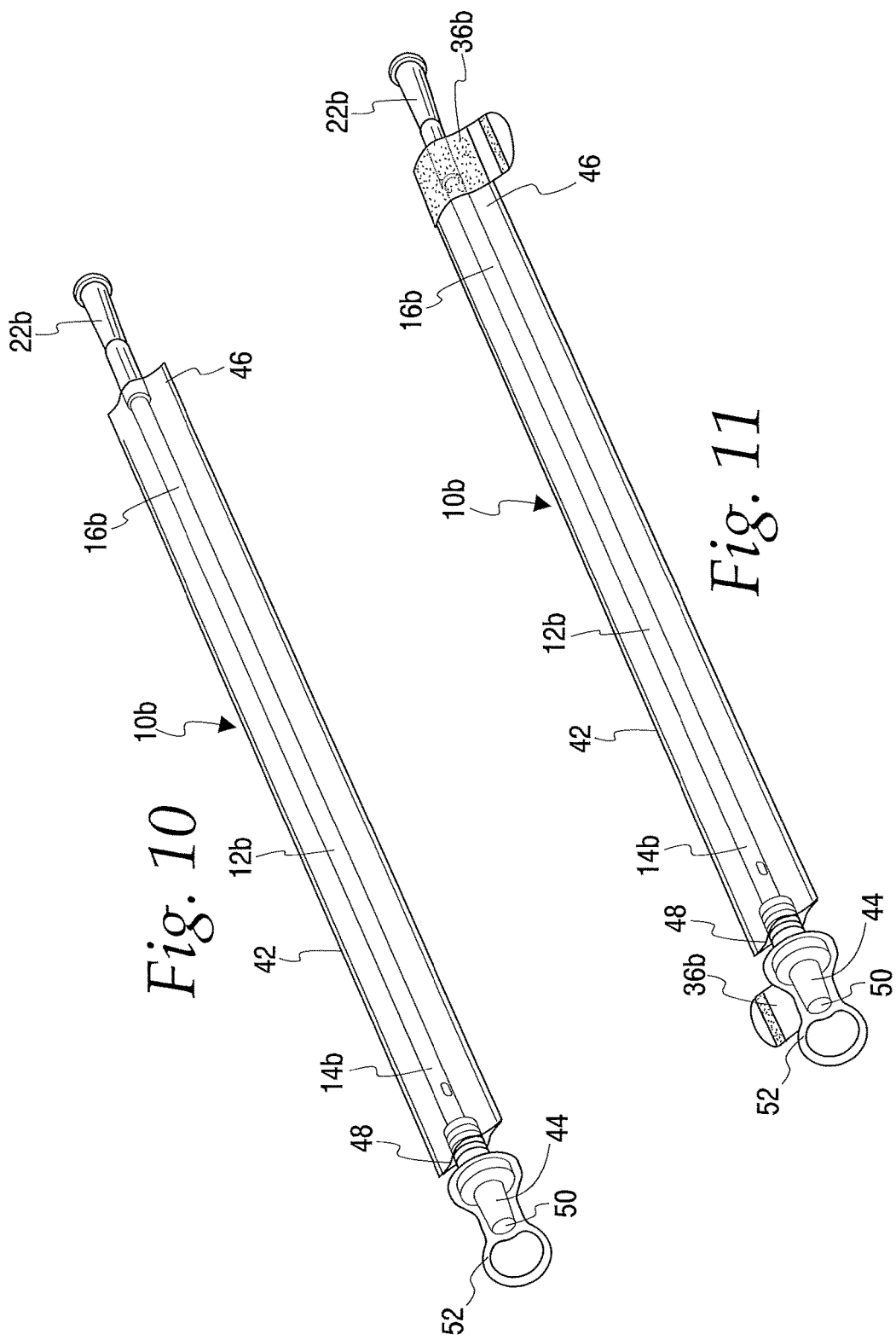

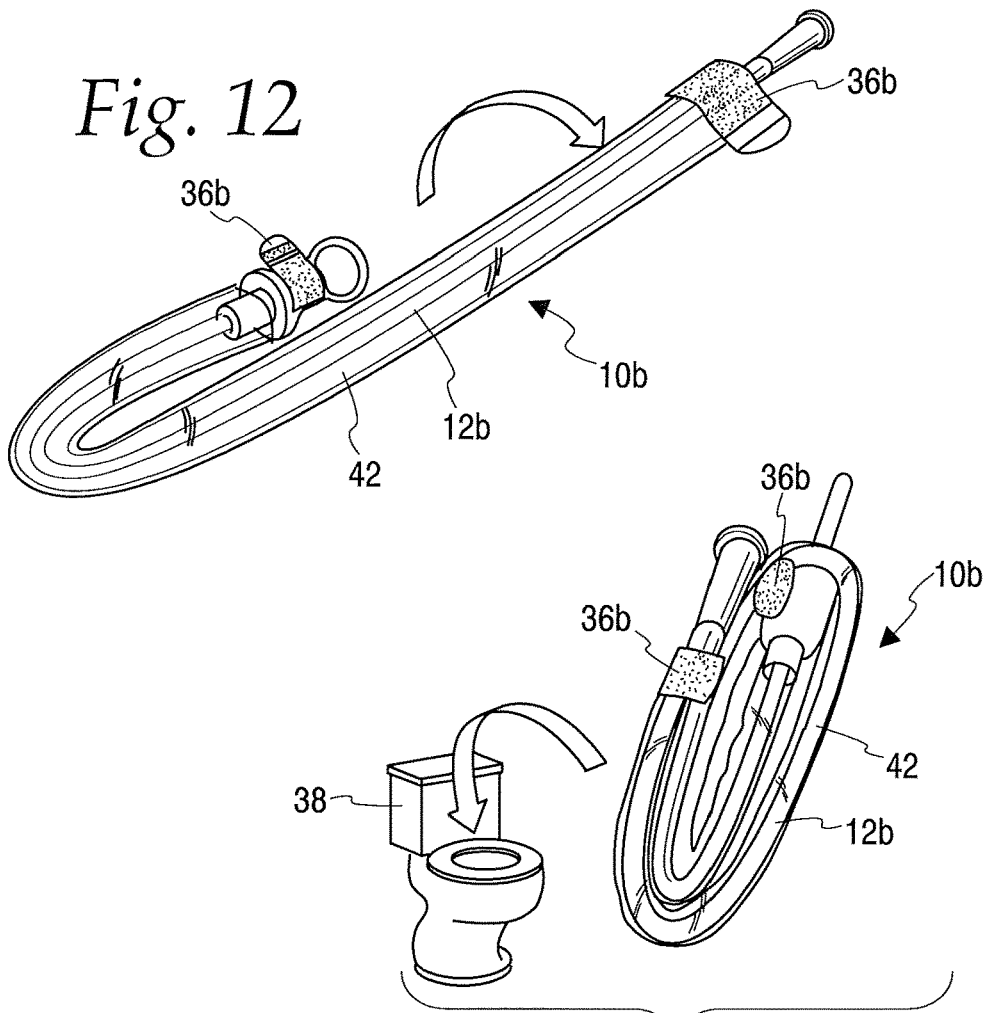
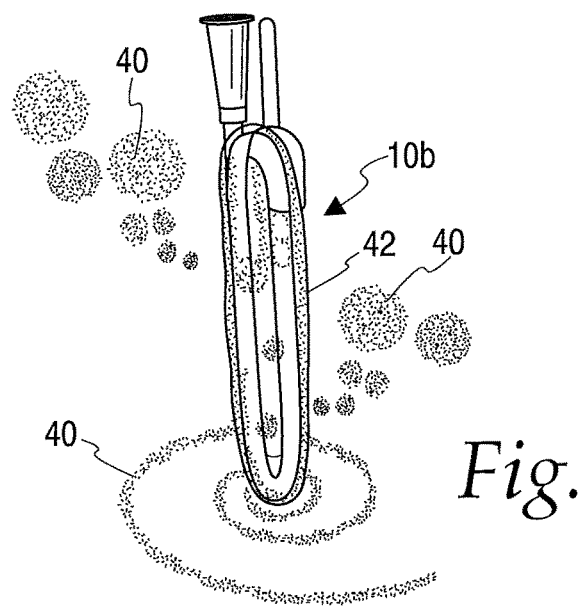
Fig. 12
Fig. 13
Fig. 14

FLUSHABLE CATHETERS

RELATED APPLICATIONS

This application is the U.S. National Stage of PCT International Patent Application No. PCT/US2014/069569, filed Dec. 10, 2014, which claims the benefit of and priority to U.S. Provisional Patent Application Ser. No. 61/915,382, filed Dec. 12, 2013; U.S. Provisional Patent Application Ser. No. 61/915,396, filed Dec. 12, 2013; and U.S. Provisional Patent Application Ser. No. 62/011,282, filed Jun. 12, 2014, all of which are hereby incorporated herein by reference.

DESCRIPTION

Field of the Disclosure

The present disclosure generally relates to flushable catheters. More particularly, the present disclosure relates to flushable catheter assemblies which may include one or more shrinkable portions that compact the catheter assembly for passage of the assembly down the toilet and through the sewer pipes.

Description of Related Art

Intermittent catheters are commonly used by those who suffer from various abnormalities of the urinary system, such as urinary incontinence. With the advent of intermittent catheters, individuals with urinary system abnormalities can self-insert and self-remove intermittent catheters several times a day. Intermittent catheterization involves inserting the elongated shaft of a catheter through the urethra and into the bladder. Urine is drained from the bladder through the catheter and into a waste receptacle, such as a toilet or collection bag.

After the bladder has been drained, the catheter is disposed of in a waste container, such as a garbage can. Sometimes, especially in a public restroom, it may be difficult to find a suitable waste container to dispose of the catheter and, if the individual has to carry the catheter some distance to a waste container, there may be some risk of leakage or spillage of bodily fluids. Additionally, the individual, especially in a public restroom, may be uncomfortable or embarrassed with carrying a used catheter to the waste container. In such situations, the individual may attempt to dispose of the catheter by flushing it down the toilet, which can cause significant plumbing problems, such as clogging. This is especially problematic for male users, as male urinary catheters are typically much longer than female urinary catheters, due to anatomical considerations. Such catheters are typically made from non-biodegradable polymeric materials, such as non-biodegradable thermoplastics, in which case flushing the catheter down the toilet also raises environmental concerns.

Accordingly, there has been increasing interest in producing flushable catheters which are made from materials that structurally breakdown when contacted with water, e.g., materials that are soluble in water, degrade in water and/or undergo hydrolysis. Such catheters are intended to be flushed down the toilet after use, and disintegrate (dissolve, and/or hydrolyse or physically degrade) or breakdown while passing through the sanitary system. Because flushable catheters are required to substantially maintain structural integrity during use (i.e., during insertion into the urethra, drainage of urine, and removal from the urethra), the disintegratable materials chosen are those with a slower degradation or solubility rate, in which case the catheter does not substantially disintegrate until after being disposed of in the sewer system for some time. Thus, when a flushable catheter is placed within the toilet for disposal, the structure of the catheter usually is still substantially intact and will remain substantially intact during flushing of the catheter for disposal thereof.

When a catheter is disposed of by flushing down a toilet, the force of the turbulent water current which occurs during flushing oftentimes does not carry or move the catheter down the toilet and into the pipes of the sanitary system and the catheter remains in the toilet bowl after flushing. The catheter may not flush down the toilet for any number of reasons. For example, the shape and size of the catheter may not be conducive for flushing down the toilet. This may be especially problematic with water-conserving low-flush or low-flow toilets. Regardless of the reason, a catheter that resists being fully flushed down the toilet may require the user to flush the toilet multiple times or leave the catheter in the toilet, which may be embarrassing, especially when using a public restroom.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

The catheter assemblies of the present disclosure may include one or more portions that shrink in size when in contact with a fluid, such as water or an aqueous mixture, to place the assembly in a compact configuration. The catheter assembly's compact configuration after water contact aids in passage of the catheter down the toilet and through the sewer system during flushing. The shrinkable portion(s) of the catheter assembly may be, for example, one or more of the catheter shaft, a protective sleeve surrounding at least a portion of the catheter shaft, a pouch containing the catheter or one or more sections of the catheter shaft, the protective sleeve and the pouch. Furthermore, the shrinkable portion(s) of the catheter assembly may be made from a material that shrinks when contacted with a fluid. For example, the shrinkable portion may be made from a shrinkable polymer that shrinks when it comes into contact with water. In one embodiment, the polymer may be polyvinyl alcohol. The polyvinyl alcohol may be amorphous or partially ordered wherein the polymer chains are stretched into a first configuration during the manufacturing of the catheter assembly. After use, the catheter assembly may be disposed of in a toilet wherein the toilet water contacts the stretched chains of polyvinyl alcohol. When contacted with the water, the stretched polymer chains transition back toward its natural state which causes the polyvinyl alcohol material to shrink.

In a first aspect, a flushable catheter assembly that includes a shrinkable portion which shrinks from a first configuration to a second smaller compact configuration when contacted with a fluid to reduce the size of the catheter assembly. The shrinkable portion may include one or more sections of a catheter shaft, protective sleeve or disposal pouch. The shrinkable portion may be a shrinkable polymer such as polyvinyl alcohol. Additionally, the entire catheter assembly or portions thereof, including the shrinkable portions, may be made from one or more water disintegratable materials.

In another aspect, a flushable catheter including a catheter shaft wherein at least a portion of the catheter shaft includes a shrinkable material that shrinks from a first configuration to a second compact configuration when contacted with fluid to reduce the size of the catheter shaft. The shrinkable portion(s) of the catheter shaft may be made from a shrinkable polymer such as polyvinyl alcohol. Additionally, the entire catheter assembly or portions thereof, including the shrinkable portions, may be made from one or more water disintegratable materials.

In yet another aspect, a flushable catheter assembly includes a catheter having a catheter shaft and a sleeve surrounding at least a portion of the catheter shaft. The sleeve being shrinkable from a first configuration to a second compact configuration when contacted with a fluid to reduce the size of the catheter assembly. The shrinkable sleeve may be made from a shrinkable polymer such as amorphous polyvinyl alcohol. Additionally, the entire catheter assembly or portions thereof, including the shrinkable portions, may be made from water disintegratable materials.

In another aspect, a flushing catheter assembly including a catheter and a pouch adapted to contain the catheter wherein the pouch shrinks from a first configuration to a second configuration when contact with a fluid to reduce the size of the catheter assembly. The shrinkable pouch may be made from a shrinkable polymer such as polyvinyl alcohol. Additionally, the entire catheter assembly or portions thereof, including the shrinkable portions, may be made from water disintegratable materials.

BRIEF DESCRIPTION OF THE DRAWINGS

FIG. 1 is a perspective view of a urinary catheter assembly according to an aspect of the present disclosure;

FIG. 2 is a schematic representation of an amorphous area of a polymer from which the catheter assembly or a portion thereof may be made;

FIG. 3 is a schematic representation of the amorphous area of the polymer of FIG. 2 wherein the polymer chains have been transitioned toward a substantially straight state;

FIG. 4 is a schematic representation of the amorphous polymer of FIG. 3 shown with the polymer chains in contact with water molecules and transitioning back toward to the amorphous state;

FIG. 5 is a cross-sectional view taken along lines 5-5 of FIG. 1 showing one alternative embodiment of the catheter assembly according to the present disclosure;

FIG. 6 is a perspective view of another embodiment of a catheter assembly according to the present disclosure;

FIG. 7 is a perspective view of the catheter assembly of FIG. 6 shown being bent into a bent configuration;

FIG. 8 is a perspective view of the catheter assembly of FIG. 6 shown in the bent configuration and being disposed of in a toilet;

FIG. 9 is a perspective view of the catheter assembly of FIG. 8 schematically shown in contact with a fluid and shrinking into a compact configuration;

FIG. 10 is a perspective view of another embodiment of a catheter assembly in accordance with the present disclosure;

FIG. 11 is a perspective view of another embodiment of a catheter assembly in accordance with the present disclosure;

FIG. 12 is a perspective view of the catheter assembly of FIG. 11 showing the catheter assembly being bent into a bent configuration;

FIG. 13 is a perspective view of the catheter assembly of FIG. 12 shown in the bent configuration and being disposed of in a toilet;

FIG. 14 is a perspective view of the catheter assembly of FIG. 13 schematically shown in contact with a fluid and shrinking into a compact configuration;

DESCRIPTION OF THE ILLUSTRATED EMBODIMENTS

Figure 15:
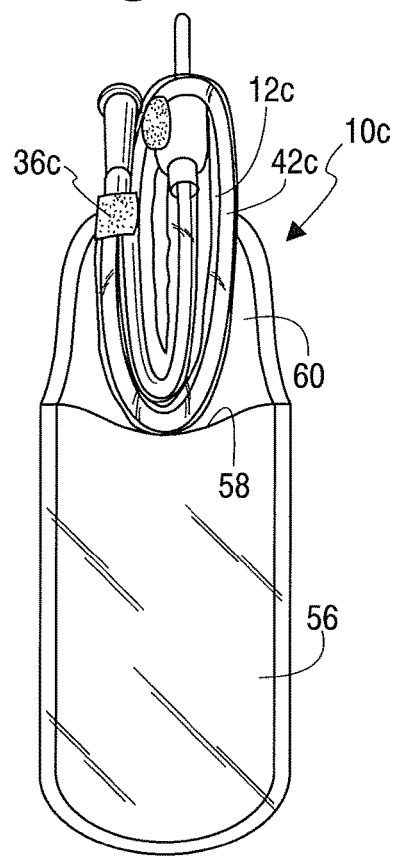
FIG. 15 is a perspective view of another embodiment of a catheter assembly in accordance with the present disclosure wherein the catheter assembly includes a pouch into which the catheter is placed in for disposal.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

FIG. 1 shows an embodiment of a flushable catheter assembly 10 according to an aspect of the present disclosure. The catheter assembly 10 includes an elongated catheter shaft 12 having a proximal end portion 14 and a distal end portion 16. The proximal end portion 14 of the catheter shaft 12 is suitable for insertion into a lumen or a passageway of the body, such as the urethra. The proximal end portion 14 may include one or more drainage holes or eyes 18 for the drainage of bodily fluids therethrough and into an internal conduit or lumen of the catheter shaft 12.

Fluid entering the catheter shaft 12 via the eye 18 flows from the proximal end portion 14 to the distal end portion 16. The distal end portion 16 may include an associated drainage member or funnel assembly 20 for fluidly connecting the flow path defined by the catheter shaft 12 to a collection container, such as a collection bag, or for directing urine into a waste container, such as a toilet.

The catheter assembly 10 or portions thereof (shaft, drainage member, etc.) preferably, but not necessarily, structurally breakdown when contacted with water for convenient disposal down the toilet and through the sewer system. The catheter assemblies and portions thereof may, for example, be made from one or more materials that are affected by a fluid (for example, water, urine or fluids utilized in toilet and plumbing systems). Such materials may be water disintegratable or disintegrable materials. As used herein "water disintegratable" or "water disintegrable" materials refer to materials that are water soluble, water degradable, or water hydrolysable and which dissolve, degrade or otherwise breakdown when in contact with water. In other embodiments, the material may be enzymatically hydrolysable. The water disintegratable and enzymatically hydrolysable materials are preferably flushable materials which are suitable for disposal in a toilet or sanitary system and, even more preferably, biodegradable flushable materials which may be chemically broken down by living organisms or other biological means.

The disintegratable or enzymatically hydrolysable materials used to construct the catheter assembly or portions thereof may include, for example, polyvinyl alcohol, including but not limited to an extrudable polyvinyl alcohol, polyacrylic acids, polylactide, polyesters, polyglycolide, poly lactide-co-glycolide, amines, polyacrylamides, poly(N-(2-Hydroxypropyl) methacrylamide), starch, modified starches or derivatives, amylopectin, pectin, xanthan, scleroglucan, dextrin, chitosans, chitins, agar, alginate, carrageenans, laminarin, saccharides, polysaccharides, sucrose, polyethylene oxide, polypropylene oxide, acrylics, polyacrylic acid blends, poly(methacrylic acid), polystyrene sulfonate, polyethylene sulfonate, lignin sulfonate, polymethacrylamides, copolymers of aminoalkyl-acrylamides and methacrylamides, melamine-formaldehyde copolymers, vinyl alcohol copolymers, cellulose ethers, poly-ethers, polyethylene oxide, blends of polyethylene-polypropylene glycol, carboxymethyl cellulose, guar gum, locust bean gum, hydroxypropyl cellulose, vinylpyrrolidone polymers and copolymers, polyvinyl pyrrolidone-ethylene-vinyl acetate, polyvinyl pyrrolidone-carboxymethyl cellulose, carboxymethyl cellulose shellac, copolymers of vinylpyrrolidone with vinyl acetate, hydroxyethyl cellulose, gelatin, poly($\varepsilon$-caprolactone), poly(p-dioxanone), polyhydroxyalkanoate or combinations, blends or co-polymers of any of the above materials. The water disintegratable or enzymatically hydrolysable materials may also be any of those that are included in certified flushable products that meet the National Sanitation Foundation standards for flushability or materials and products that meet INDA/EDANA Flushability Guidelines or the UK Water Industry Research test protocols set forth in "Test Protocol to Determine the Flushability of Disposable Products, Review of the Manufactures $3^{rd}$ Ed. Guidance Document," 2013, by Drinkwater et al. While catheters made from water disintegratable or enzymatically hydrolysable materials may be disposed of in a toilet, it is not necessary to dispose of such catheters in a toilet and such catheters may also be disposed in normal municipal waste systems or garbage collection systems.

Additionally, the catheter assembly 10 or portions thereof may be made from a flushable disintegratable material that is also shrinkable, such as a shrinkable water disintegratable (degradable/soluble/hydrolysable) polymer. The catheter assembly or portion(s) thereof can be made from the shrinkable material shrink in order to aid in passage of the catheter assembly down the toilet and through the sewer pipes during flushing. As used herein, the term "shrink" refers to the reduction or lessening in size by contracting or contraction of a material in one or more dimensions. When the shrinkable material shrinks, the catheter assembly changes from a first configuration for use during bladder drainage to a second compact configuration which aids in disposal of the catheter down the toilet.

In one embodiment of the catheter assembly 10, the catheter shaft 12 or portions thereof may be made of a shrinkable material. Such shrinkable material may be a shrinkable polymer which is also a water disintegratable polymer. The shrinkable polymer may also be a polymer that shrinks when placed in contact with a fluid, such as water. For example, when placed in a toilet and in contact with toilet water.

In one embodiment, the shrinkable polymer may be an amorphous polymer or a polymer that includes amorphous regions, i.e., polymer chains oriented randomly, and/or intertwined. The polymer also may be a semi-crystalline polymer or a polymer that has semi-crystalline regions. FIG. 2 shows a schematic representation of an amorphous region 22 of a polymer having polymer chains 24 that are oriented randomly and/or are intertwined. Turning to FIG. 3, during preparation of the polymer and/or manufacture the catheter assembly, the polymer chains 24 are moved into a more orientated state or toward a more semi-crystalline/crystalline state by straightening the polymer chains, which lengthens or otherwise increases the size of the polymer material. Straightening of the polymer chains and setting the chains to remain in the more straighten state may be achieved by stretching the polymer, e.g. stretching a tube formed of the polymer, while at an elevated temperature and then rapidly cooling the polymer. Referring to FIG. 4, when the stretched polymer chains 24 come into contact with water molecules 26, the water molecules 26 diffuse into the polymer chains 24. The water molecules 26 may serve as a plasticizer that reduces the glass transition ($T_g$) of the polymer. Lowering the glass transition enhances the mobility of the polymer chains 24 which results in the polymer chains 24 of the amorphous region 22 to transition back toward their natural or near natural configuration. As the polymer chains 24 transition back toward their natural configuration the polymer material shrinks.

Referring back to FIGS. 2 and 3, the amorphous region 22 may be transformed into more orientated state by, for example, mechanical stretching to at least partially straighten out and/or orientate the polymer chains. When mechanical stretching of the polymer material is employed, the polymer chains at least partially straighten in the direction of stretching. Other methods for transforming the amorphous region to an orientated state may include cold stretching post (as oppose to during) manufacturing the tubes, or stretching under controlled temperature and humidity environment such as curing and drawing.

As mentioned above, the catheter shaft 12 may be a shrinkable shaft that is made of a polymer, such as a water disintegratable extrudable polyvinyl alcohol. In one embodiment of manufacturing the catheter shaft 12, the amorphous region of the polymer from which the catheter shaft 12 is made is transitioned toward a more orientated state by stretching the amorphous polymer during the extrusion process. In one embodiment of the extrusion process, heated polyvinyl alcohol is extruded and stretched to form a stretched tube. The tube is then rapidly cooled to lock the polymer chains in a stretched state. In this process, the polymer material may be stretched about 3 to about 5 times its initial size, for example. After the stretched tube has been cooled, the tube may be cut to the desired length of the catheter shaft. Preferably, the stretched tube may be kept away from excessive exposure to humidity or moisture or temperature. An insertion tip is formed at the proximal end of the shaft and a drainage member is added to the distal end.

Referring to FIG. 5, the inner and outer surfaces 28, 30 of the catheter shaft 12 may, optionally, be coated with water disintegratable barrier layers 32, 34 that prevent fluids, such as urine or moisture on the user's hands, from initially contacting the shaft 12 and/or slows the rate at which the fluid contacts the shaft 12. The barrier layer 32, 34 prevents or limits the amount of shrinkage of the catheter shaft 12 during use, i.e., during catheter insertion into and withdrawal from the urethra and drainage of the bladder. Optionally, the outer barrier layer 34 may also serve as a lubricant or may be a lubricant that aids in easing insertion of the catheter shaft 12 into and withdrawal of the catheter from the urethra. In other embodiments, a lubricant separate from the outer barrier layer 34 may be applied over the barrier layer 34. In one exemplary embodiment, the inner and outer surfaces 28, 30 of the shrinkable catheter shaft 12 are coated with oleophilic lubricants that serve as both barrier layers 32, 34 and a lubricant. When the catheter assembly is placed into the toilet and in contact with water for disposal, with time, the water disintegrates the barrier layers and/or seeps past the barrier layers and contacts the shrinkable material to cause the material to shrink.

In yet another embodiment, the catheter shaft 12 may be made by coextruding multiple layers wherein all of the layers are made from flushable polymers, which may also be shrinkable. For example, a coextruded shaft may have three layers including an inner layer, an outer layer and an intermediate layer wherein the inner and outer layers are made from different grades of water disintegratable polymers than the intermediate layer. The inner and outer layers may have different rates of degradation/solubility from each other and/or from the intermediate layer. For example, the inner and outer layers may be made from polyvinyl alcohols with different, slower rates of solubility as compared to the rate of solubility of the intermediate layer. The inner layer, which defines the lumen of the catheter, and the outer layer, which defines the outer surface of the catheter shaft, may provide a barrier that prevents and/or slows fluid from contacting the intermediate faster disintegratable and/or shrinkable layer while the catheter is being used to drain the bladder. The inner and outer layers may be made, for example, from a water degradable/soluble polymer that does not substantially disintegrate during bladder drainage or slowly degrades/dissolves during drainage. When the catheter is disposed of in the toilet and in contact with water, the water comes in contact with the inner and outer layers first and then seeps through to the intermediate layer, which disintegrates and/or shrinks at a relatively faster rate than the inner and/or outer layers.

When catheter assembly 10 is used to drain the bladder, the proximal end 12 of the catheter shaft is inserted into the urethra until it enters the bladder. Urine is then drained from the bladder through shaft 12 and into a waste collection receptacle such as a urine collection bag or a toilet. In one embodiment, the urine collection bag may also be made from a flushable water disintegratable material. After the bladder has been sufficiently drained, the user removes the catheter shaft 12 from the urethra and disposes of the catheter shaft 12 in the toilet. The water in the toilet dissolves or seeps past the barrier layers (if present) and contacts the catheter shaft 12. The catheter shaft 12 shrinks into a more compact configuration which aids in flushing of the catheter shaft down the toilet and through the pipes. In one embodiment, the catheter shaft 12 shrinks from about 3 to 5 times its original size (its pre-use size). The user may throw the catheter in the toilet in its elongated configuration or, alternatively, the user may knot, bend or wind the catheter prior to throwing it into the toilet. While the catheter is in the sewer system, the water within the sewer system disintegrates (dissolves, degrades and/or hydrolyses) the catheter.

FIGS. 6 and 7 illustrate another embodiment of a shrinkable, flushable catheter assembly 10a in accordance with the present disclosure. In this embodiment, the catheter assembly 10a may include one or more securing members 36, such as an adhesive, a strap or string, for securing the catheter assembly 10a in a wound or bent configuration after use and prior to disposal in the toilet. In the illustrated embodiment, the securing member 36 is shown as being attached to the distal end 16a of the catheter shaft 12a. The securing member 36 may be attached during manufacture or may be attached by the user after use. When the securing member 36 is attached by the user, the user may attach the securing member anywhere along the catheter shaft 12a and funnel 20a. Turning to FIGS. 7 and 8, after the catheter assembly 10a has been used to drain the bladder, the user winds or bends the catheter shaft 12a and employs the securing member 36 to secure the catheter shaft 12a in the wound or bent configuration. After the catheter assembly 10a has been secured, it is placed in a toilet 38 for disposal thereof. Referring to FIG. 9, when placed within the toilet, the catheter shaft 12a comes into contact with water 40, which causes the catheter shaft 12a to shrink, placing the catheter assembly 10a into a compact configuration. In the compact configuration, it may be easier for the catheter assembly 10a to pass through the drain and trapway/u-bend pipe of the toilet and through the sewer pipes. While in the sewer system the water disintegratable material of catheter assembly 10a continues to disintegrate (dissolve, degrade or hydrolyse) until it is substantially disintegrated.

FIGS. 10-12 illustrate another embodiment of a catheter assembly 10b in accordance with present disclosure. The catheter assembly 10b includes an elongated catheter shaft 12b having a proximal insertion end portion 14b and a distal end portion 16b. The proximal end portion 14b of the catheter shaft 12b is suitable for insertion into a lumen or a passageway of the body, such as the urethra.

The catheter assembly 10b also includes a protective sleeve 42 and an introducer tip 44. The protective sleeve 42 surrounds at least a portion of the catheter shaft 12b to separate and enclose the portion of the catheter shaft 12b from the outside environment. Furthermore, the user may grasp the catheter shaft 12b through the protective sleeve 42 to handle and manipulate the catheter assembly 10b. The protective sleeve 42 may have a distal end 46 that is attached to a distal end portion 16b of the catheter shaft 12b or to the funnel 22b. A proximal end 48 of protective sleeve 42 is attached to the introducer tip 44. The introducer tip 44 includes slits 50 that open to allow passage of catheter shaft 12b therethrough during insertion of the catheter shaft 12b into the urethra. The catheter assembly 10b may also include a removable introducer tip cap 52 that covers and protects the introducer tip 44. The protective sleeve 42, introducer tip 44, introducer tip cap 52, catheter shaft 12b, funnel 22b, and any other portions of catheter assembly 10b may be made of any of the water disintegratable and/or shrinkable materials disclosed herein and may be disposed of by flushing down the toilet.

In one embodiment, the protective sleeve 42 may be made from a shrinkable material that shrinks when the material comes into contact with a fluid, such as water. The shrinkable material may be made from, for example, a water shrinkable polymer. In one embodiment, the sleeve 42 is made from a polymer film which as has been stretched to orientate the polymer chains. When the polymer comes into contact with water, its stretched chains gains mobility and transition back toward their natural state which results in shrinkage of the polymer film. The polymer film may be, for example, made from a polyvinyl alcohol that shrinks when placed in contact with water.

As illustrated in FIG. 11, catheter assembly 10b may, optionally, include one or more securing members 36b that may be used for securing the catheter assembly 10b in a bent or wound configuration prior to disposal within the toilet. Such securing elements 36b may be adhesives tabs, straps, strings or any other suitable securing element that can hold the catheter assembly 10b in a bent or wound configuration. In the illustrated embodiment, catheter assembly 10b includes securing members 36b located at the proximal and distal ends of the catheter assembly 10b wherein one securing element 36b is associated with the introducer tip cap 52 and the other securing element 36b is associated with the distal end portion 46 of the sleeve 42. In other embodiments, the catheter assembly 10b may include one securing element or more than two securing elements. Additionally, the securing elements 36b may be positioned at any suitable location on the catheter assembly 10b.

When the catheter assembly is used to drain the bladder of a patient, the introducer tip cap 52 is removed to expose the introducer tip 44. The exposed introducer tip 44 is then inserted into the urethral opening of the patient. The patient then grasps the catheter shaft 12b through the protective sleeve 42 to advance the catheter shaft 12b through the slit or opening 50 in the introducer tip 44 to advance the catheter shaft 12b into the urethra. The catheter shaft 12b may be pre-lubricated or the user may apply lubricant to the catheter shaft 12b to ease insertion of the catheter shaft 12b into the urethra. The lubricant may be, for example, polyethylene glycol, propylene glycol, glycerol, hydrophilic coatings or an oleophilic substance, such as an oleated glycerol (glycerol mono, di, tri or mixed oleates), oleyl alcohol, oleic acid, and mixtures thereof. As the catheter shaft 12b is advanced into the urethra of the patient, the sleeve 42 may bunch or crumple at or toward the distal end 16b of the catheter shaft 12b. After urine has been drained from the bladder, the patient removes the catheter from the urethra of the patient and extends the sleeve 42 back over the catheter shaft 12b.

With the sleeve 42 extended back over the catheter shaft 12b, the user may place the catheter assembly 10b directly into the toilet for disposal. Optionally, the user may wind or knot the catheter assembly 10b prior to disposal in the toilet. When the catheter assembly includes securing elements 36b, the catheter assembly 10b may be bent or wound and secured in the bent or wound configuration, as illustrated in FIGS. 12 and 13. Referring to FIG. 14, when placed in the toilet 38, the sleeve 42 comes into contact with water 40 which causes the sleeve 42 to shrink. In one embodiment, the sleeve 42 shrinks 3 to 5 times its original size (its pre-use size). The shrinkage of the sleeve 42 places the catheter assembly 10b into a compact configuration for flushing down the toilet 38 and across the trapway/u-bend pipe. In one alternative embodiment, catheter shaft 12b may also be made from a shrinkable material that also shrinks when contacted by water, such as catheter shaft 12 described above. As mentioned above, catheter assembly 10b may be made from water disintegratable materials and the catheter assembly continues to disintegrate within the sewer system until it is completely dissolved or hydrolysed.

Figure 16:
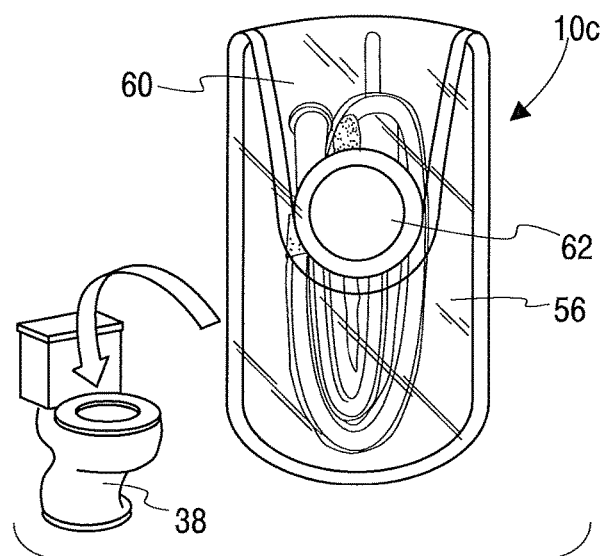
FIG. 16 is a perspective view of the catheter assembly of FIG. 15 shown with the catheter folded within the pouch and being disposed of in the toilet.
Figure 17:
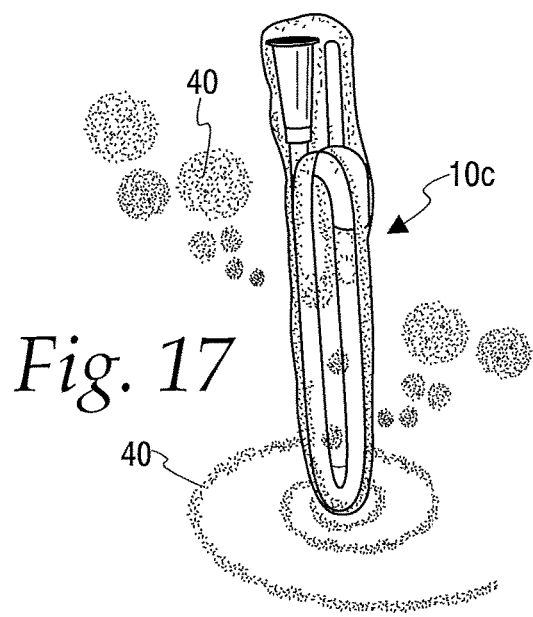
FIG. 17 is a perspective view of the catheter assembly of FIG. 16 schematically shown in contact with a fluid and shrinking into a compact configuration.

FIGS. 15-17 illustrate another embodiment of a catheter assembly 10c in accordance with the present disclosure. In this embodiment, the catheter assembly 10c includes a flushable pouch 56 that may be made from any of the water disintegratable materials disclosed herein, which may or may not be shrinkable. In one embodiment, the pouch 56 may be made from any of the shrinkable, flushable material disclosed herein. For example, the pouch 56 may be made from a shrinkable polymer film that shrinks when the film comes into contact with a fluid, such as water. In one embodiment, the shrinkable polymer film is a stretched polymer which has been stretched to straighten the polymer chains. When the polymer comes into contact with water, the polymer chains transition back toward their natural state which causes the material to shrink.

Referring to FIGS. 15 and 16, after the catheter assembly 10c has been used to drain the bladder and the user is ready to dispose of the catheter assembly 10c, the user bends or winds the catheter shaft 12c and places it into pouch 56. In the illustrated embodiment, the pouch 56 includes an opening 58 for accepting the catheter therein and a flap 60 for closing the opening of the pouch 56. The pouch 56 may include a closing element 62, such as an adhesive, for securing the flap 60 in a closed position. Also in the illustrated embodiment, the catheter assembly 10c is shown including a protective sleeve 42c and securing elements 36c. It will be understood that the sleeve 42c and securing elements 36c are optional and that the pouch 56 may be used to dispose of a catheter assembly that does not include such elements. Furthermore, the shaft 12c and the sleeve 42c of catheter assembly 10c also may, optionally, be made from shrinkable material as described above.

Turning to FIGS. 16 and 17, after the catheter assembly 10c has been placed in the pouch 56, it is disposed of in the toilet 38 where it comes into contact with water 40. When contacted within water 40, the pouch 56 shrinks to place the catheter assembly 10c into a compact configuration which may make it easier for the catheter assembly 10c to be flushed down the toilet and across the trapway/u-bend of the sewer pipes. In one embodiment, the pouch 56 shrinks 3 to 5 times its original size (its pre-use size). As the catheter assembly 10c passes through the sewer system, the water of the system disintegrates the water disintegratable materials of the catheter assembly until the catheter assembly 10c is substantially dissolved, degraded or hydrolysed.

FIGS. 18-23 illustrate another embodiment of a catheter assembly 10d in accordance with the present disclosure. In this embodiment, the catheter assembly 10d includes a urine collection bag 70 for collecting urine drained from the bladder. Prior to use of the catheter assembly 10d, the catheter 12d may be located within the urine collection bag 70. In other embodiments, the catheter 12d and urine collection bag 70 may be provided separately. The collection bag 70 also may include an insertion aid 72 and cap 74 associated therewith. The insertion aid 72 and cap 74 are similar to those shown in FIGS. 10 and 11. The insertion aid may be used to insert the catheter into the urethra. The inserted catheter is used to drain urine from the bladder into the urine collection bag 70.

After catheterization has been completed, urine within the collection bag 70 may be emptied into the toilet through a tear open opening 76, which may be a perforation or weakened portion of the walls of the urine collection bag 70. After the urine has been emptied from the collection bag 70, the catheter 12d may be placed back into the urine collection bag 70 for disposal of the catheter assembly down the toilet. In other words, the urine collection bag 70 may become a catheter disposal pouch.

The urine collection bag 70 and the catheter 12d may be made of any of the flushable, water disintegratable materials disclosed herein, which may or may not be shrinkable. In one embodiment, the urine collection bag 70 and the catheter 12d are made from any of the shrinkable, flushable materials disclosed herein.

Figure 18:
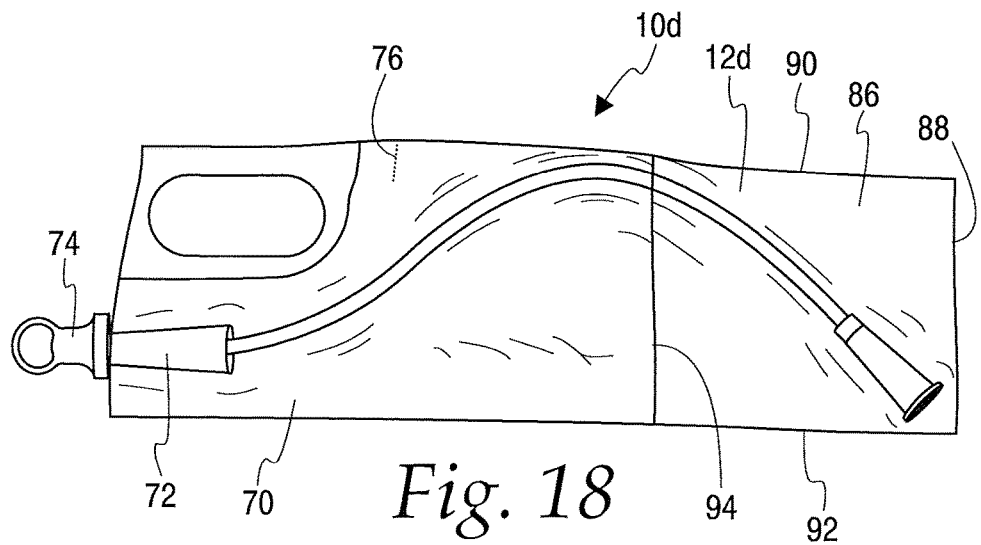
FIG. 18 is a perspective view of another embodiment of a catheter assembly in accordance with the present disclosure wherein the catheter assembly includes a urine collection bag into which the catheter can be placed for disposal thereof.
Figure 18A:
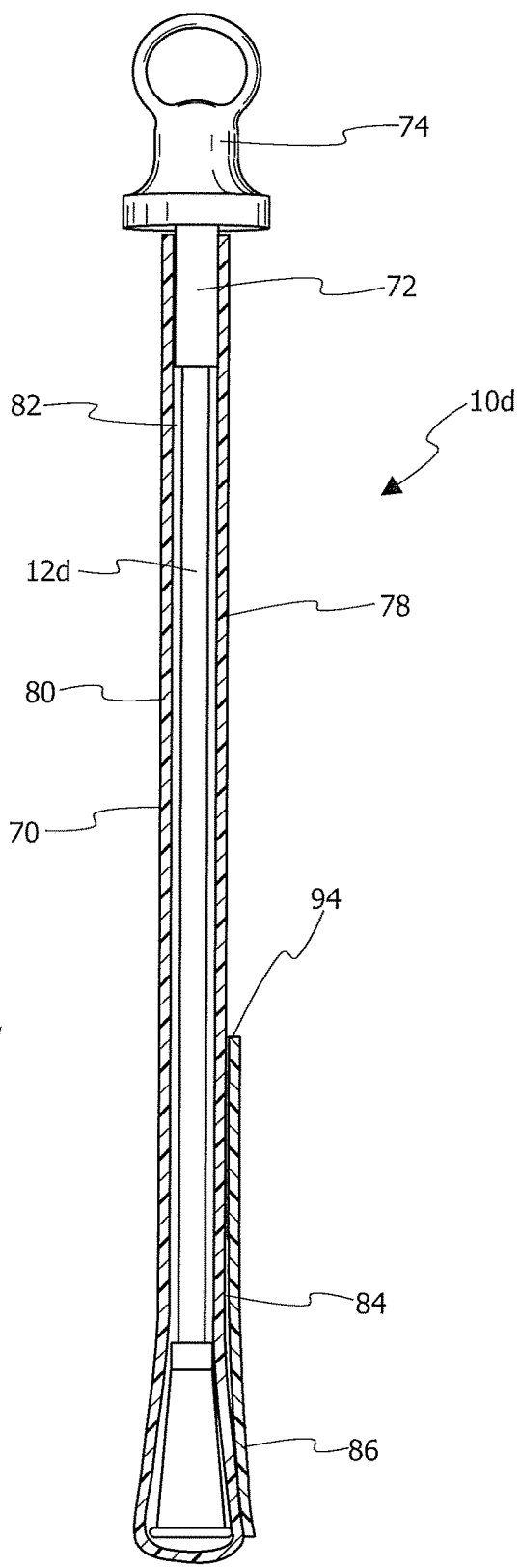
FIG. 18a is a cross-sectional view of the catheter assembly of FIG. 18.

Referring to FIG. 18a, the urine collection bag 70 may include a front wall 78 and a rear wall 80 which are sealed together about their periphery to define a urine collection chamber 82. The collection bag 70 may also include a pocket 84 on the exterior of the collection bag 70. In the illustrated embodiment, the pocket 84 is associated with the front wall 78. In other embodiments, the pocket 84 may be associated with the rear wall 80. The pocket 84 may be defined between the front wall 78 of the urine collection bag 70 and a sheath or film 86 extending at least partially over a portion of the front wall 78. In the illustrated embodiment, the sheath 86 extends over a bottom portion of the front wall 78 of the urine collection bag 70 and is attached to the urine collection bag 70 along three sides of the sheath 86. In particular, the sheath 86 is attached to the front wall 78 along the bottom 88 and opposing sides 90, 92 of the sheath 86. The top 94 of the sheath 86 is unattached to define an opening of the pocket 84 as shown in FIGS. 18 and 18a. The collection bag 70 and/or the sheath 86 forming the pocket 84 may be made from a shrinkable polymer film that shrinks when the sheath 86 comes into contact with a fluid, such as water.

Figure 19:
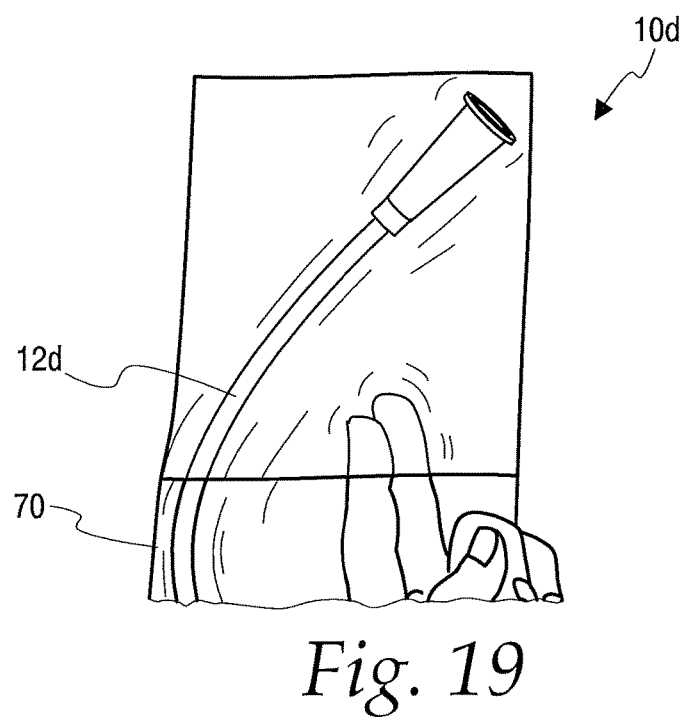
FIGS. 19-22 are perspective views showing the process of folding the urine collection bag of FIG. 18 into a compact configuration for disposal down the toilet.
Figure 20:
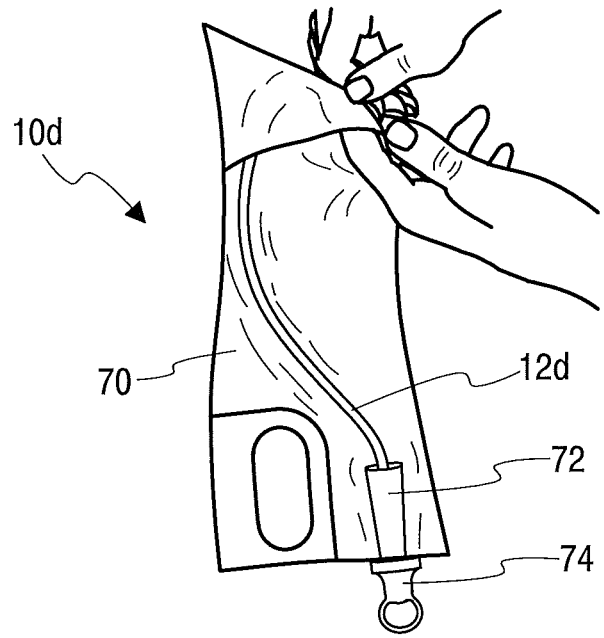
Figure 21:
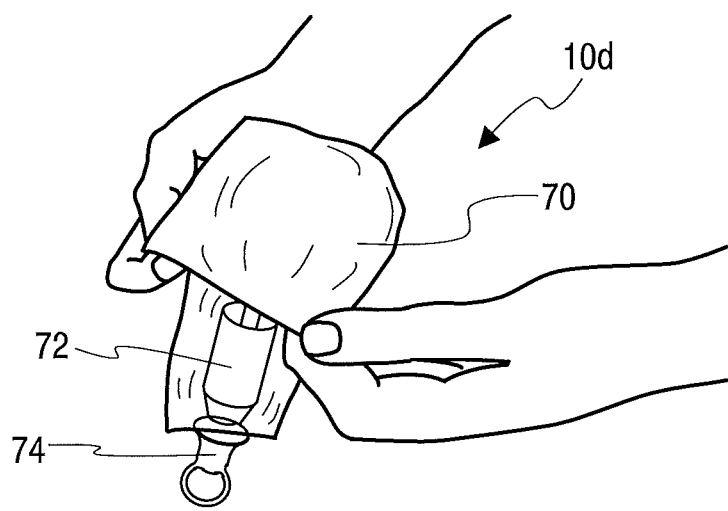
Figure 22:
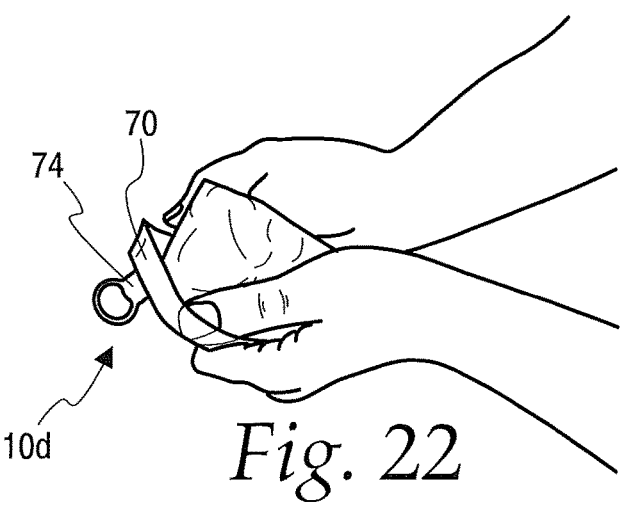
Figure 23:
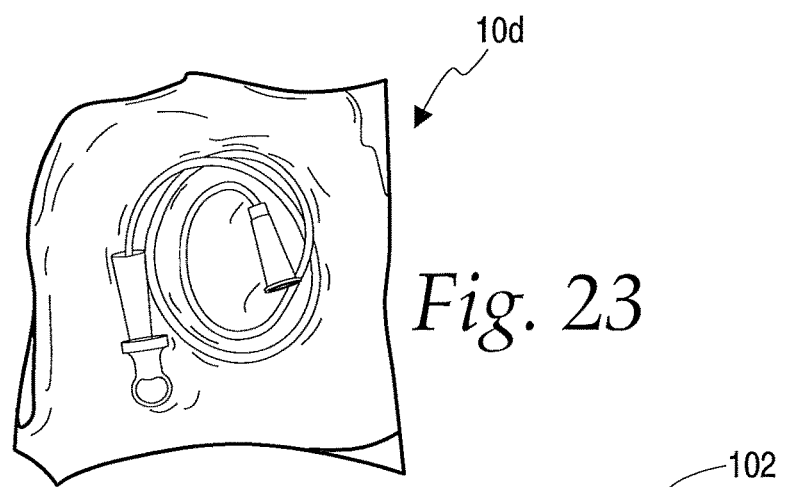
FIG. 23 is a perspective view of the urine collection bag of FIG. 18 shown in the folded compact figuration.

Referring to FIGS. 19-23, after the urine collection bag 70 is emptied, the catheter 12d is placed back into the collection bag 70 and the collection bag 70 having the catheter 12d therein is folded into the pocket 84 for compact disposal of the catheter assembly 10d. In particular, the user may open the pocket 84 and invert it to turn the pocket inside out, as shown in FIGS. 19 and 20. The user may then fold the reminder of the collection bag 70 into the inverted pocket, as shown in FIGS. 21 and 22. In other embodiments, the collection bag 70 may be gathered into or placed into pocket 84 in other manners. For example, pocket 84 is not inverted and collection bag 70 may be rolled or gathered into pocket 84. Referring to FIG. 23, the catheter assembly 10d is now in a compact configuration for disposal thereof. If the catheter assembly 10d is made from a flushable material, the now compact assembly 10d may be flushed down the toilet.

Figure 24:
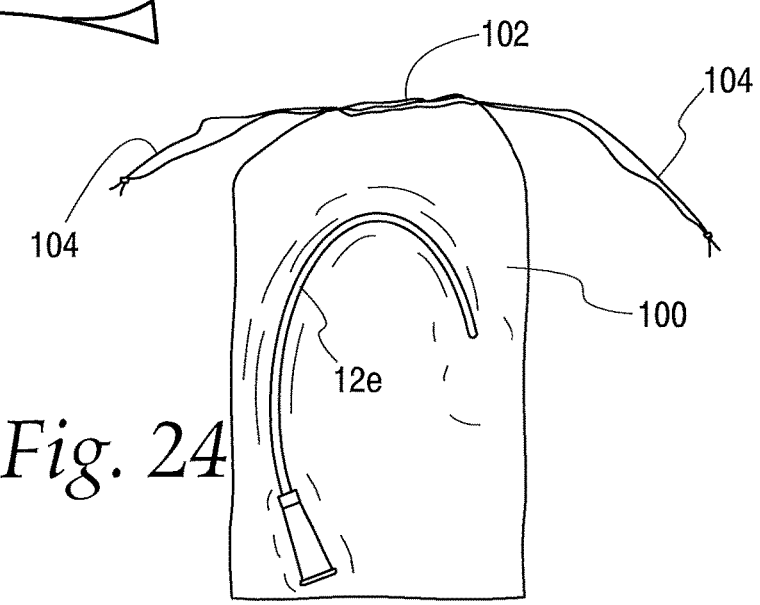
FIG. 24 is a perspective view of another embodiment of a flushable catheter assembly of the present disclosure.

FIG. 24 illustrates another embodiment disposal pouch 100 for disposing of a spent catheter 12e. The pouch 100 has an opening 102 in the top for placement of the catheter 12e therein. The pouch 100 may also include drawstrings 104 that may be pulled to cinch the opening 102 into a closed position. The pouch 100, drawstrings 104 and/or the catheter 12e may be made from any of the above-mentioned flushable and/or shrinkable materials. When made of a flushable, shrinkable material, the user places the pouch 100 having the catheter 12e therein into a toilet for disposal thereof. In the toilet water, the material of the pouch 100 shrinks into a compact configuration for passage through the sewer system where the catheter 12e and pouch 100 are dissolved or degraded by the water of the sewer system.

Figure 25:
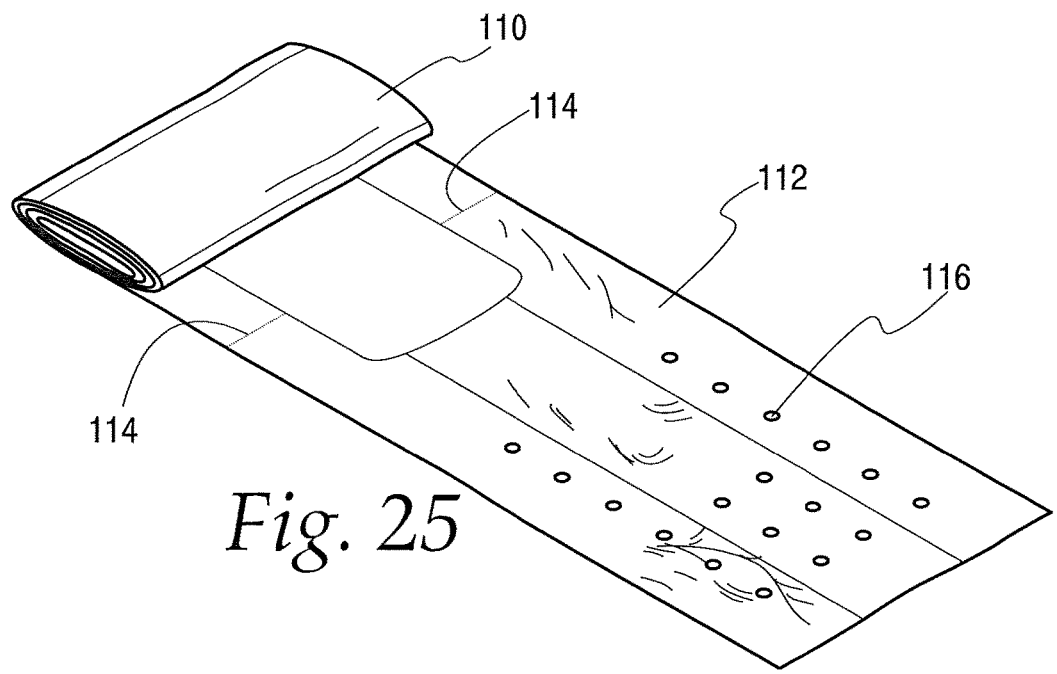
FIG. 25 is a perspective view of one embodiment of a supply of flushable disposal pouches in accordance with the present disclosure.
Figure 26:
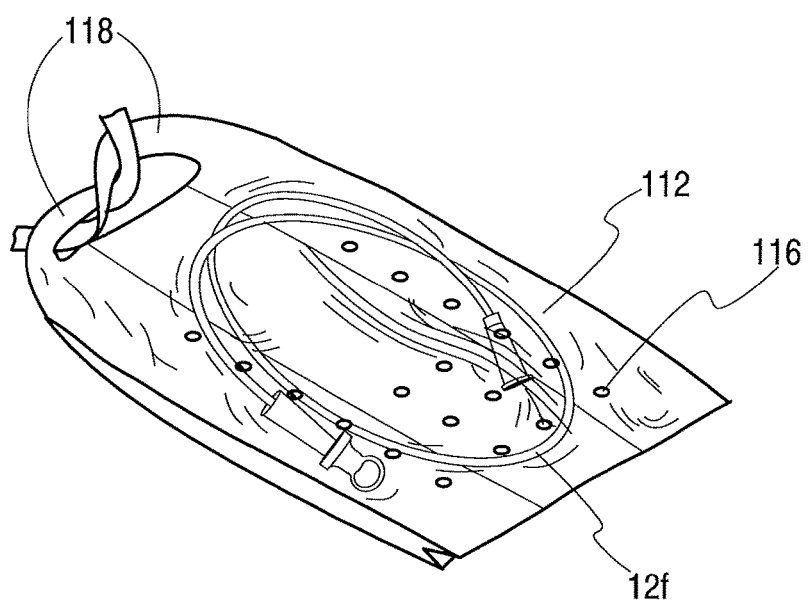
FIG. 26 is a perspective view of a disposal pouch containing a catheter for disposal thereof down the toilet.

FIG. 25 illustrates one embodiment of a supply 110 of flushable disposal pouches 112 for disposal of a spent catheter 12f. In this embodiment, the supply 110 may be in the form of a roll of disposal pouches 112. As shown in this figure, the disposal pouches 112 may be connected to adjacent pouches by a perforation 114. The user tears the perforation 114 to remove a pouch 112 from the supply roll 110. The user then places the catheter 12f into the disposal pouch 114 for disposal of the catheter 12f. The pouch 112 may include a plurality of holes 116 through the wall of the pouch to allow air to be pushed out of the pouch 114 so that the pouch 114 can be easily compressed about the catheter 12f. The holes 16 also allow water allow water to flow therethrough so that the water may contact the catheter prior to degradation of the pouch 112. The pouch 112 may also include handles 118 that may be tied to secure the catheter 12f within pouch 112.

It may be advantageous for the catheter assembly and/or its individual components (shaft, funnel, and/or introducer cap) to have a selected density and/or buoyancy for improving the flow of the catheter assembly through the pipes of a sewage system. For example, it may be preferred for the catheter assembly and/or its individual components to have a density in the range of approximately 0.4 $g/cm^3$ to approximately 1.2 $g/cm^3$ when in the compact configuration, although it is also within the scope of the present disclosure for the catheter assembly or one or more of its individual components to have a density that is outside of this range. More preferably, the catheter shaft, funnel, and/or introducer cap assembly may have a density in the range of approximately 0.68 $g/cm^3$ to approximately 0.89 $g/cm^3$ when in the compact configuration. Such densities may be advantageous in causing the catheter assembly in the compact configuration to assume a particular orientation and/or to rest at a particular depth in water or self-orientate in a certain direction to facilitate flushing, but it is within the scope of the present disclosure for the catheter shaft, funnel, and/or introducer cap assembly to have a different density and/or for different portions of the catheter shaft, funnel, and/or introducer cap assembly to have different densities/buoyancies.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

OTHER ASPECTS

Aspect 1. A flushable catheter assembly comprising:
a shrinkable portion which shrinks from a first configuration to a second smaller compact configuration when contacted with a fluid to reduce the size of the catheter assembly.

Aspect 2. The catheter assembly of aspect 1, wherein the shrinkable portion comprises a catheter shaft.

Aspect 3. The catheter assembly of aspect 1 further including a catheter shaft and a sleeve extending over at least a portion of the catheter shaft wherein the shrinkable portion comprises the sleeve.

Aspect 4. The catheter assembly of aspect 1 further including a catheter shaft and a pouch for containing the catheter shaft wherein the shrinkable portion comprises the pouch.

Aspect 5. The catheter assembly of aspect 4 wherein the pouch is a urine collection bag.

Aspect 6. The catheter assembly of aspect 4 wherein the pouch includes a wall having a plurality of holes.

Aspect 7. The catheter assembly of any one of aspects 4-6 wherein the pouch includes a pocket into which the pouch may be gathered.

Aspect 8. The catheter assembly of one of the proceeding aspects wherein the shrinkable portion is made from a polymer.

Aspect 9. The catheter assembly of aspect 8 wherein the polymer comprises a stretched polymer when in the first configuration.

Aspect 10. The catheter assembly of any one of the proceeding aspects wherein the shrinkable portion is made from a water disintegratable polymer.

Aspect 11. The catheter assembly of aspect 10 wherein the water disintegratable polymer comprises one or more of a water soluble polymer, a water hydrolysable polymer and an enzyme hydrolysable polymer.

Aspect 12. The catheter assembly of any one of the proceeding aspects wherein the shrinkable portion is made from polyvinyl alcohol.

Aspect 13. The catheter assembly of aspect 12 wherein the polyvinyl alcohol comprises amorphous or semi-crystalline polyvinyl alcohol.

Aspect 14. A flushable catheter, comprising:
a catheter shaft wherein at least a portion of the catheter shaft comprises a shrinkable material that shrinks from a first configuration to a second compact configuration when contacted with fluid to reduce the size of the catheter shaft.

Aspect 15. The catheter assembly of aspect 14 wherein the catheter shaft has an inner surface and an outer surface, and a barrier layer or coating overlies at least one of the inner surface and the outer surface.

Aspect 16. The catheter assembly of aspect 15 wherein a first barrier layer or coating overlies the inner surface and a second barrier layer or coating overlies the outer surface.

Aspect 17. The catheter assembly of any one of aspects 15-16 wherein the barrier layer comprises a lubricant for easing insertion of the catheter shaft into the urethra.

Aspect 18. The catheter assembly of aspect 14 wherein the catheter shaft comprise multiple coextruded layers.

Aspect 19. The catheter assembly of aspect 18 wherein the catheter shaft comprises an outer layer, an inner layer and an intermediate layer therebetween, and the intermediate layer being made of the shrinkable material.

Aspect 20. The catheter assembly of aspect 19 wherein the outer and inner layers are made from a water disintegratable material.

Aspect 21. The catheter assembly of aspect 14 further including a pouch for containing the catheter shaft wherein the pouch is also at least partially made of a shrinkable material.

Aspect 22. The catheter assembly of one of aspects 14-21 wherein the shrinkable material is a polymer.

Aspect 23. The catheter assembly of aspect 22 wherein the polymer comprises a stretched polymer when in the first configuration.

Aspect 24. The catheter assembly of any one of aspects 14-23 wherein the material is made from a water disintegratable polymer.

Aspect 25. The catheter assembly of aspect 24 wherein the water disintegratable polymer comprises one or more of a water soluble polymer, a water hydrolysable polymer and an enzyme hydrolysable polymer.

Aspect 26. The catheter assembly of any one of aspects 14-25 wherein the shrinkable portion is made from polyvinyl alcohol.

Aspect 27. The catheter assembly of aspect 26 wherein the polyvinyl alcohol comprises amorphous or semi-crystalline polyvinyl alcohol.

Aspect 28. A flushable catheter assembly, comprising:
a catheter having a catheter shaft;
a sleeve surrounding at least a portion of the catheter shaft wherein the sleeve shrinks from a first configuration to a second compact configuration when contacted with a fluid to reduce the size of the catheter assembly.

Aspect 29. The catheter assembly of aspect 28 further including a pouch for containing the catheter shaft and sleeve wherein the pouch also shrinks from a first configuration to a second compact configuration when contacted with a fluid.

Aspect 30. The catheter assembly of one of aspects 28-29 wherein the sleeve is made from a shrinkable polymer.

Aspect 31. The catheter assembly of aspect 30 wherein the polymer comprises a stretched polymer when in the sleeve is in the first configuration.

Aspect 32. The catheter assembly of any one of aspects 28-31 wherein the catheter assembly is made from a water disintegratable polymer.

Aspect 33. The catheter assembly of aspect 32 wherein the water disintegratable polymer comprises one or more of a water soluble polymer, a water hydrolysable polymer and an enzyme hydrolysable polymer.

Aspect 34. The catheter assembly of any aspects 28-33 wherein the sleeve is made from polyvinyl alcohol.

Aspect 35. The catheter assembly of aspect 34 wherein the polyvinyl alcohol comprises an amorphous or semi-crystalline polyvinyl alcohol.

Aspect 36. A flushing catheter assembly, comprising:
a catheter;
a pouch adapted to contain the catheter wherein the pouch shrinks from a first configuration to a second configuration when contact with a fluid to reduce the size of the catheter assembly.

Aspect 37. The catheter assembly of aspect 36 wherein the pouch is made from a shrinkable polymer.

Aspect 38. The catheter assembly of aspect 37 wherein the polymer comprises a stretched polymer when in the pouch is in the first configuration.

Aspect 39. The catheter assembly of any one of aspects 36-38 wherein the catheter assembly is made from a water disintegratable polymer.

Aspect 40. The catheter assembly of aspect 39 wherein the water disintegratable polymer comprises one or more of a water soluble polymer, a water hydrolysable polymer and an enzyme hydrolysable polymer.

Aspect 41. The catheter assembly of any aspects 36-40 wherein the sleeve is made from polyvinyl alcohol.

Aspect 42. The catheter assembly of aspect 41 wherein the polyvinyl alcohol comprises an amorphous or semi-crystalline polyvinyl alcohol.

The invention claimed is:

1. A flushable catheter assembly comprising:
a shrinkable catheter shaft that contracts in size from a first configuration to a second smaller compact configuration when contacted with a fluid to reduce the size of the catheter shaft; and
wherein the shrinkable catheter shaft comprises a stretched amorphous polymer that includes straightened polymer chains that are conditioned to transition from a straightened state in the first configuration to a more amorphous state in the second configuration.

2. The catheter assembly of claim 1 further including a sleeve extending over at least a portion of the catheter shaft.

3. The catheter assembly of claim 1 further including a pouch for containing the catheter shaft wherein the pouch comprises shrinkable material.

4. The catheter assembly of claim 3 wherein the pouch is a urine collection bag.

5. The catheter assembly of claim 3 wherein the pouch includes a wall having a plurality of holes.

6. The catheter assembly of claim 3 wherein the pouch includes a pocket into which the pouch may be gathered.

7. The catheter assembly of claim 1 wherein the catheter shaft is made from a water disintegratable polymer.

8. The catheter assembly of claim 7 wherein the water disintegratable polymer comprises one or more of a water soluble polymer, a water hydrolysable polymer and an enzyme hydrolysable polymer.

9. The catheter assembly of claim 1 wherein the shrinkable catheter shaft is made from polyvinyl alcohol.

10. A flushable catheter, comprising:
 a catheter shaft wherein at least a portion of the catheter shaft comprises a shrinkable material that contracts in size from a first configuration to a second compact configuration when contacted with fluid to reduce the size of the catheter shaft; and
 the shrinkable material comprising a stretched amorphous polymer that includes straightened polymer chains that are conditioned to transition from a straightened state in the first configuration to a more amorphous state in the second configuration.

11. The catheter assembly of claim 10 wherein the catheter shaft has an inner surface and an outer surface, and a barrier layer or coating overlies at least one of the inner surface and the outer surface.

12. The catheter assembly of claim 11 wherein a first barrier layer or coating overlies the inner surface and a second barrier layer or coating overlies the outer surface.

13. The catheter assembly of claim 11 wherein the barrier layer comprises a lubricant for easing insertion of the catheter shaft into the urethra.

14. The catheter assembly of claim 10 wherein the catheter shaft comprises multiple coextruded layers.

15. The catheter assembly of claim 14 wherein the catheter shaft comprises an outer layer, an inner layer and an intermediate layer therebetween, and the intermediate layer being made of the shrinkable material.

16. The catheter assembly of claim 15 wherein the outer and inner layers are made from a water disintegratable material.

17. The catheter assembly of claim 10 further including a pouch for containing the catheter shaft wherein the pouch is also at least partially made of a shrinkable material.

18. The catheter assembly of claim 10 wherein the shrinkable material is made from a water disintegratable polymer.

19. The catheter assembly of claim 18 wherein the water disintegratable polymer comprises one or more of a water soluble polymer, a water hydrolysable polymer and an enzyme hydrolysable polymer.

20. The catheter assembly of claim 10 wherein the shrinkable material is made from polyvinyl alcohol.

* * * * *